United States Patent
Takada

(10) Patent No.: US 11,298,299 B2
(45) Date of Patent: Apr. 12, 2022

(54) METHOD FOR PREPARING OIL-IN-WATER TYPE EMULSION COMPOSITION, AND COSMETIC MATERIAL

(71) Applicant: SHIN-ETSU CHEMICAL CO., LTD., Tokyo (JP)

(72) Inventor: Yuko Takada, Annaka (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 53 days.

(21) Appl. No.: 16/647,357

(22) PCT Filed: Sep. 7, 2018

(86) PCT No.: PCT/JP2018/033205
§ 371 (c)(1),
(2) Date: Mar. 13, 2020

(87) PCT Pub. No.: WO2019/054292
PCT Pub. Date: Mar. 21, 2019

(65) Prior Publication Data
US 2021/0154105 A1   May 27, 2021

(30) Foreign Application Priority Data
Sep. 14, 2017 (JP) .............................. JP2017-176648

(51) Int. Cl.
*A61K 8/06* (2006.01)
*A61Q 1/04* (2006.01)
*A61K 8/891* (2006.01)

(52) U.S. Cl.
CPC .............. *A61K 8/06* (2013.01); *A61K 8/891* (2013.01); *A61Q 1/04* (2013.01)

(58) Field of Classification Search
None
See application file for complete search history.

(56) References Cited

U.S. PATENT DOCUMENTS

| | | | |
|---|---|---|---|
| 5,061,481 A | 10/1991 | Suzuki et al. | |
| 6,534,590 B1 | 3/2003 | Aso et al. | |
| 7,862,895 B2 * | 1/2011 | Kamei | A61K 8/895 |
| | | | 428/405 |
| 2007/0237731 A1 | 10/2007 | De Oliveira Praes | |
| 2011/0256077 A1 | 10/2011 | Hayakawa | |
| 2013/0011454 A1 | 1/2013 | Park et al. | |
| 2018/0280283 A1 | 10/2018 | Kojima et al. | |

FOREIGN PATENT DOCUMENTS

| | | | |
|---|---|---|---|
| EP | 0 388 582 A2 * | 9/1990 | |
| EP | 0 388 582 A2 | 9/1990 | |
| EP | 0388582 * | 9/1990 | |
| JP | 7-187951 A | 7/1995 | |
| JP | 2784730 B2 | 1/1998 | |
| JP | 2844077 B2 | 1/1999 | |
| JP | 2001-226222 A | 8/2001 | |
| JP | 2002-47129 A | 2/2002 | |
| JP | 4757991 B2 | 8/2011 | |
| JP | 2012-153802 A | 8/2012 | |
| JP | 2012-206971 A | 10/2012 | |
| JP | 5533176 B2 | 6/2014 | |
| JP | 5943801 B2 | 7/2016 | |
| WO | WO 2017/061099 A1 | 8/2018 | |

OTHER PUBLICATIONS

Extended European Search Report dated May 18, 2021, in European Patent Application No. 18855791.2.
International Search Report (PCT/ISA/210) issued in PCT/JP2018/033205, dated Nov. 27, 2018.
Okamoto, Formulation technology learned from cosmetics-based technology: The 2nd formulation technology used in skin care cosmetics, Pharm Tech Japan, 2006, vol. 22, No. 9. pp. 1711-1715.
Written Opinion (PCT/ISA/237) issued in PCT/JP2018/033205, dated Nov. 27, 2018.

* cited by examiner

*Primary Examiner* — Danah Al-Awadi
(74) *Attorney, Agent, or Firm* — Birch, Stewart, Kolasch & Birch, LLP

(57) ABSTRACT

Provided is a method for preparing an oil-in-water type emulsion composition, the method comprising a step for stirring and emulsifying a composition containing components (A), (B), (C) and (D) below and then treating under a high shear pressure of 30-300 Mpa, wherein (A) is 5-35 mass % of an acrylic-silicone graft copolymer, (B) is 5-35 mass % of volatile oil, (C) is 2-15 mass % of polyoxyethylene sorbitan fatty acid ester having average addition mole number of ethylene oxide (EO) of 10 or more and HLB of 11 or more, and (D) is 15-88 mass % of water.

6 Claims, No Drawings

METHOD FOR PREPARING OIL-IN-WATER TYPE EMULSION COMPOSITION, AND COSMETIC MATERIAL

TECHNICAL FIELD

The present invention relates to a method for preparing oil-in-water emulsion compositions containing an acrylic-silicone graft copolymer.

BACKGROUND ART

Film-forming agents which are water resistant and oil resistant so as to impart good properties to cosmetic films and which prevent makeup from coming off have been developed in the field of makeup cosmetics, including lipstick, eye makeup such as mascara, and skin care products. Silicone oils and silicone resins having water repellency are commonly used as such film-forming agents, the important qualities of which are to keep makeup from wearing off and give it excellent longevity. Examples of water-repelling silicone oils and silicone resins used in cosmetic preparations include crosslinked silicones obtained by the addition polymerization of a silicone resin or an organohydrogenpolysiloxane with a vinyl group-containing organopolysiloxane, and acrylic-silicone graft copolymers. Of these, acrylic-silicone graft copolymers are widely used because they are soft films and have excellent water repellency (Patent Document 1: JP No. 2704730).

In recent years, owing to concerns over environmental impact and irritation of the skin, not only acrylic-silicone graft copolymer-containing water-in-oil cosmetic preparations, but also acrylic-silicone graft copolymer-containing oil-in-water emulsion cosmetic preparations, are commonly used in makeup cosmetics (Patent Document 2: JP No. 2844077; Patent Document 3: JP No. 5533176; Patent Document 4: JP No. 5943801). In order to include an acrylic-silicone graft copolymer in an oil-in-water cosmetic, it is necessary to emulsify the acrylic-silicone graft copolymer in the oil-in-water system. However, oil-in-water emulsion compositions of acrylic-silicone graft copolymers have a poor shelf stability and may give rise to concentration separation over time. Also, due to the influence of surfactants, there is a possibility of a decrease in water resistance, a decrease in film formability, and of irritation of the skin and bitterness.

Although investigations of oil-in-water emulsion compositions of acrylic-silicone graft copolymers have hitherto been carried out, in most oil-in-water emulsion compositions of acrylic-silicone graft copolymers that form a film having water resistance, acrylic polymerization is carried out in water. In such a production method, acrylic monomer remains within the composition, making it unsuitable for cosmetic preparations (Patent Document 5: JP No. 4757991).

Hence, although there exists a desire for oil-in-water emulsion compositions of acrylic-silicone graft copolymers which can be used in cosmetic preparations, form a soft, water-resistant film, are mild to the skin, and have minimal bitterness and a good shelf stability, there have hitherto been no reports on methods for producing such oil-in-water emulsion compositions.

PRIOR ART DOCUMENTS

Patent Documents

Patent Document 1: JP No. 2704730
Patent Document 2: JP No. 2844077
Patent Document 3: JP No. 5533176
Patent Document 4: JP No. 5943801
Patent Document 5: JP No. 4757991

SUMMARY OF INVENTION

Technical Problem

In light of the above circumstances, the object of this invention is to provide an acrylic-silicone graft copolymer-containing oil-in-water emulsion composition which can be used in cosmetic preparations, has good coating properties and film formability, forms a film having water resistance and the softness characteristic of acrylic-silicone graft copolymers, is mild to the skin, and has minimal bitterness and a good shelf stability.

Solution to Problem

The inventor has conducted extensive investigations in order to achieve this object and discovered as a result that the above problems can be resolved by agitating and thereby emulsifying a composition containing specific amounts of (A) an acrylic-silicone graft copolymer, (B) a volatile oil, (C) a polyoxyethylene sorbitan fatty acid ester having an average number of added moles of ethylene oxide (EO) of at least 10 and a hydrophilic-lipophilic balance (HLB) of at least 11 and (D) water, and subsequently treating the emulsified composition under a high shear pressure of from 30 to 300 MPa. This discovery ultimately led to the present invention. Treatment under a high shear pressure results in an even better shelf stability and good coating properties. When an acrylic-silicone graft copolymer-containing oil-in-water emulsion composition obtained by the production method of the invention is used in a cosmetic preparation, a film forms that has water resistance and the softness characteristic of acrylic-silicone graft copolymers. Also, because the bitterness is minimal, the oil-in-water emulsion composition obtained by the inventive production method is gentle on the body and suitable for skin care applications, especially lipstick applications.

Accordingly, the invention provides the following method for producing oil-in-water emulsion compositions and the following cosmetic preparation.

[1] A method for producing an oil-in-water emulsion composition, which method includes the steps of:

agitating and thereby emulsifying a composition containing:

(A) from 5 to 35 wt % of an acrylic-silicone graft copolymer which has a weight-average molecular weight of 3,000 to 100,000 and contains constituent units (1) and (2) of the following general formulas

[Chem. 1]

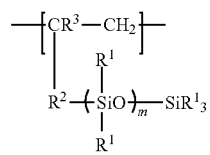

(1)

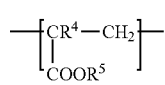

(wherein each $R^1$ is a group independently selected from monovalent hydrocarbon groups, $R^2$ is an alkyleneoxycarbonyl group of 2 to 11 carbon atoms (the alkylene group being limited to a structure that bonds with a silicon atom), $R^3$ and $R^4$ are each independently a hydrogen atom or a methyl group, $R^5$ is an alkyl group of 1 to 22 carbon atoms or a hydrogen atom, m is an integer from 3 to 500, and the molar ratio between the constituent units having general formulas (1) and (2), expressed as (1)/(2), is from 0.02 to 1), (B) from 5 to 35 wt % of a volatile oil, (C) from 2 to 15 wt % of a polyoxyethylene sorbitan fatty acid ester having an average number of moles of added ethylene oxide (EO) of at least 10 and a hydrophilic-lipophilic balance (HLB) of at least 11, and (D) from 15 to 88 wt % of water; and subsequently treating the emulsified composition under a high shear pressure of from 30 to 300 MPa.

[2] The method for producing an oil-in-water emulsion composition of [1], wherein component (C) is one or more selected from the group consisting of polyoxyethylene sorbitan monolaurate, polyoxyethylene sorbitan monostearate, polyoxyethylene sorbitan monooleate and polyoxyethylene sorbitan monopalmitate.

[3] The method for producing an oil-in-water emulsion composition of [1] or [2], wherein emulsion particles in the oil-in-water emulsion composition have an average particle size of 300 nm or less.

[4] The method for producing an oil-in-water emulsion composition of any of [1] to [3], wherein component (B) is a volatile oil selected from the group consisting of silicone oils having a viscosity at 25° C. of 2 mm²/s or less and hydrocarbon oils.

[5] The method for producing an oil-in-water emulsion composition of any of [1] to [4], further including the step of including (E) a water-soluble polymer compound in an amount, based on the combined amount of components (A) and (B), of from 0.1 to 5 wt %.

[6] A cosmetic preparation which includes the oil-in-water emulsion composition obtained by the production method of any of [1] to [5].

Advantageous Effects of Invention

The production method of the invention makes it possible to provide acrylic-silicone graft copolymer-containing oil-in-water emulsion compositions which can be used in cosmetic preparations, have good coating properties and film formability, form a film having water-resistance and the softness characteristic of acrylic-silicone graft copolymers, is mild to the skin, and has minimal bitterness and a good shelf stability.

DESCRIPTION OF EMBODIMENTS

The invention is described in detail below.

[Component (A)]

Component (A) is an acrylic-silicone graft copolymer which contains constituent units (1) and (2) of the general formulas shown below and has a molecular weight of from 3,000 to 100,000. More specifically, it is a copolymer obtained by grafting polysiloxane chains to an acrylic polymer chain. Component (A) may be of one type used alone or of two or more types used in suitable combination.

[Chem. 2]

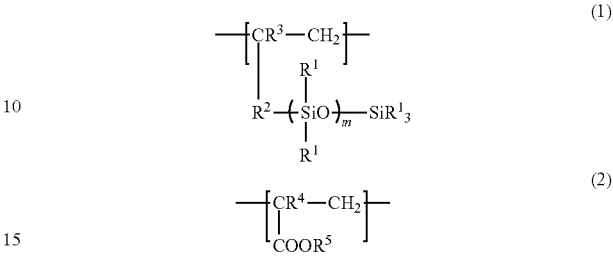

(In these formulas, each $R^1$ is a group independently selected from monovalent hydrocarbon groups, $R^2$ is an alkyleneoxycarbonyl group of 2 to 11 carbon atoms (the alkenylene group being limited to a structure that bonds with a silicon atom), $R^3$ and $R^4$ are each independently a hydrogen atom or a methyl group, $R^5$ is an alkyl group of 1 to 22 carbon atoms or a hydrogen atom, and m is an integer from 3 to 500. The molar ratio of the constituent units having general formulas (1) and (2), expressed as (1)/(2), is from 0.02 to 1.)

In the above formulas, each $R^1$ is a group independently selected from monovalent hydrocarbon groups. These are exemplified by linear or branched, substituted or unsubstituted alkyl groups of 1 to 20 carbon atoms, aryl groups of 6 to 20 carbon atoms and aralkyl groups of 7 to 20 carbon atoms. Specific examples of linear or branched, substituted or unsubstituted alkyl groups of 1 to 20 carbon atoms include methyl, ethyl, propyl, isopropyl, butyl, isobutyl, tert-butyl, pentyl, neopentyl, hexyl, octyl, nonyl, decyl, undecyl, dodecyl and tridecyl groups; and halogen-substituted alkyl groups or fluorine-substituted alkyl groups such as chloromethyl, chloropropyl, bromoethyl and trifluoropropyl groups.

Examples of aryl groups of 6 to 20 carbon atoms include phenyl, tolyl, xylyl and naphthyl groups. Examples of aralkyl groups of 7 to 20 carbon atoms include benzyl, phenylethyl and phenylpropyl groups. These may be substituted. Of the above, alkyl groups of 1 to 20 carbon atoms and aryl groups are preferred. From the standpoint of versatility, methyl groups are more preferred.

$R^2$ is an alkyleneoxycarbonyl group of 2 to 11 carbon atoms (the alkylene group being limited to a structure that bonds with a silicon atom). An alkyleneoxycarbonyl group of 3 or 4 carbon atoms is preferred.

$R^3$ and $R^4$ are each independently a hydrogen atom or a methyl group. $R^5$ is an alkyl group of 1 to 22 carbon atoms or a hydrogen atom, and is exemplified by linear or branched, substituted or unsubstituted alkyl groups. Specific examples include alkyl groups such as methyl, ethyl, propyl, isopropyl, butyl, isobutyl, tert-butyl, pentyl, neopentyl, hexyl, octyl, nonyl, decyl, undecyl and dodecyl groups; and halogen-substituted alkyl groups such as chloromethyl, chloropropyl, bromoethyl and trifluoropropyl groups. Of these, an alkyl group of 1 to 10 carbon atoms or a hydrogen atom is preferred. An alkyl group of 1 to 6 carbon atoms or a hydrogen atom is more preferred.

The subscript "m" is an integer from 3 to 500, and preferably from 5 to 100. When m is less than 3, the water resistance of the formed film is inadequate; when it exceeds 500, the glass transition point of the resulting acrylic-silicone graft copolymer is too low, as a result of which a film of a sufficient strength cannot be formed.

The molar ratio of the constituent units of general formulas (1) and (2), expressed as (1)/(2), is from 0.02 to 1, preferably from 0.04 to 0.8, and more preferably from 0.05 to 0.7. When this molar ratio (1)/(2) is less than 0.02, the water resistance of the film may decrease; on the other hand, when it is larger than 1, the film becomes viscous and a film of sufficient strength cannot be formed.

The sum of constituent units (1) and (2) may be 100 mol %, although optional constituent units may be included within a range that does not detract from the advantageous effects of the invention. For example, radical polymerizable silane compound of general formula (3) may be included as such constituent units. When such constituent units are included, the amount thereof may be set to from 0 to 10 mol % of all the constituent units.

[Chem. 3]

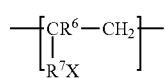

(3)

(In the formula, $R^6$ is a hydrogen atom or a methyl group, each $R^7$ is independently an alkyleneoxycarbonyl group of 2 to 11 carbon atoms, and X is a hydrolyzable silyl group of general formula (4) below.)

[Chem. 4]

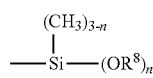

(4)

(wherein $R^8$ is a monovalent hydrocarbon group and n is an integer from 1 to 3, with the proviso that when n is 2 or 3, the $R^8$ groups may mutually differ.)

$R^8$ is exemplified in the same way as $R^1$ above, with an alkyl group of 1 to 10 carbon atoms being preferred.

Component (A) has a weight-average molecular weight of from 3,000 to 100,000, preferably from 5,000 to 100,000, and more preferably from 5,000 to 60,000. The glass transition point is preferably from −30 to +60° C. At a molecular weight below 3,000, the film durability decreases; on the other hand, at a molecular weight above 100,000, the feel upon use when the composition is included in a cosmetic preparation worsens. The weight-average molecular weight, which is determined by gel permeation chromatography (GPC), is obtained by dissolving component (A) in toluene and calculation as a polystyrene-equivalent value.

Examples of component (A) include, but are not limited to, those shown below. Copolymerization of constituent units (1) and (2) may be random, block or graft polymerization.

[Chem. 5]

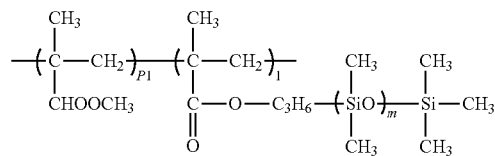

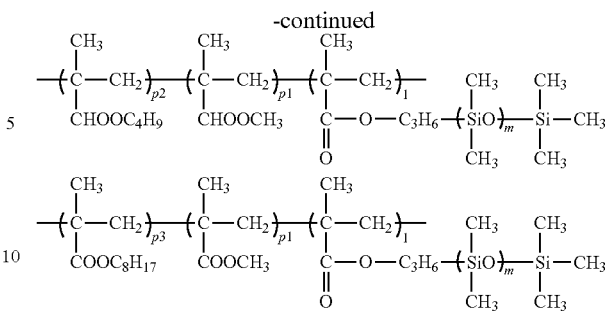

(wherein p1, p2 and p3 are integers from 0 to 50, with the sum p1+p2+p3 being from 1 to 50; and m is an integer from 3 to 500.)

[Chem. 6]

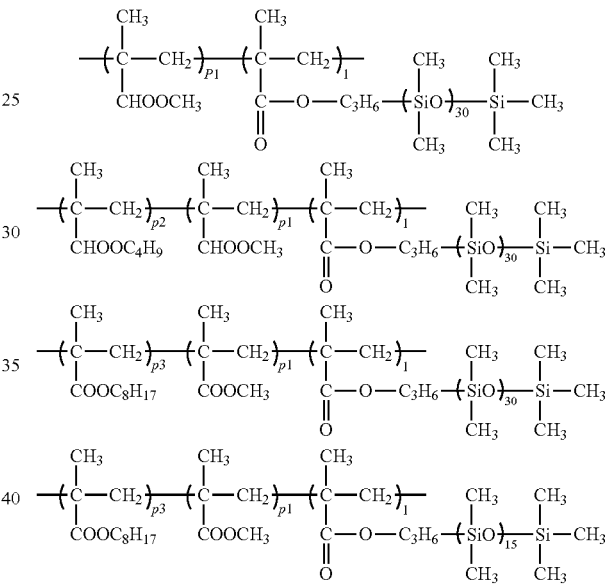

(wherein, p1, p2 and p3 are integers from 0 to 50, with the sum p1+p2+p3 being from 1 to 50.)

The acrylic-silicone graft copolymer of component (A) can be obtained by, for example, reacting a radical polymerizable group-containing organopolysiloxane compound with an acrylic monomer. From the standpoint of the ease of production and molecular design, it is preferable to use the so-called macromonomer method which copolymerizes a radical polymerizable group-containing organopolysiloxane compound of general formula (5) and an acrylic monomer of general formula (6) in the presence of a radical polymerization initiator.

[Chem. 7]

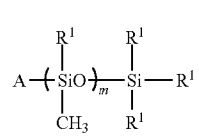

(5)

(wherein $R^1$ and m are the same as above, and A is a radical-polymerizable group of general formula (7) below.)

[Chem. 8]

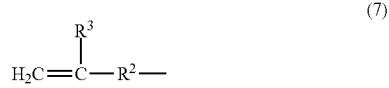
(7)

(wherein $R^2$ and $R^3$ are the same as above.)

[Chem. 9]

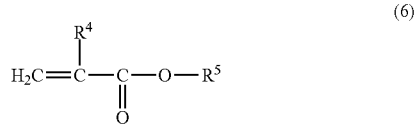
(6)

(wherein $R^4$ and $R^5$ are the same as above.)

As for the method of preparing the compound of general formula (5), this compound can be obtained by, for example, carrying out a dehydrochlorination or dechlorination reaction in accordance with the customary method on an acryloxy or methacryloxy group-substituted chlorosilane compound of general formula (8) below and a mono-terminally reactive diorganopolysiloxane of general formula (9) below.

[Chem. 10]

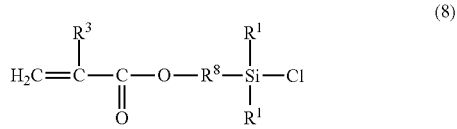
(8)

(wherein $R^3$ is the same as above and $R^8$, which is the alkylene residue of $R^2$, is a saturated divalent hydrocarbon group of 1 to 10 carbon atoms that has a linear or branched carbon chain.)

[Chem. 11]

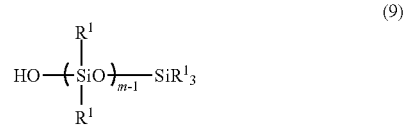
(9)

(wherein $R^1$ and m are the same as above.)

The acrylic monomer of general formula (6) which is composed primarily of acrylate and/or methacrylate is a compound having one radical polymerizable unsaturated bond on the molecule. Illustrative examples include methyl (meth)acrylate, ethyl (meth)acrylate, isopropyl (meth)acrylate, n-butyl (meth)acrylate, t-butyl (meth)acrylate, cyclohexyl (meth)acrylate, 2-ethylhexyl (meth)acrylate, tridecyl (meth)acrylate, stearyl (meth)acrylate, isostearyl (meth) acrylate and behenyl (meth)acrylate. These may be used singly or two or more may be suitably combined and used. The use in combination of methyl (meth)acrylate and, of the above monomers, a monomer that gives a homopolymer having a high glass transition temperature (Tg) and a monomer that gives a homopolymer having a low Tg is preferred.

Next, a method for preparing the acrylic-silicone graft copolymer of general formula (1) is described. An exemplary method is that of copolymerizing a radical polymerizable group-containing organopolysiloxane compound of general formula (5) with an acrylic monomer of general formula (6) in the presence of a radical polymerization initiator. This is carried out in the presence of, as the radical polymerization initiator, an ordinary radical polymerization initiator such as a peroxide (e.g., benzoyl peroxide, dicumyl peroxide, t-butylperoxy-2-ethylhexyl hexanoate) or an azo compound (e.g., azobisisobutyronitrile). The amount of radical polymerization initiator used may be an ordinary amount and is preferably from 0.01 to 5.00 wt % of the total amount of monomer that takes part in copolymerization. This amount is suitably selected according to the specified reaction rate, the degree of polymerization of the target copolymer and the type of radical polymerization initiator. Use may be made of solution polymerization, emulsion polymerization, suspension polymerization or bulk polymerization as the method of copolymerization in this invention. Of these, solution polymerization is especially preferred because it is easy to adjust the molecular weight of the resulting copolymer within an optimal range.

Solvents that may be used in this copolymerization reaction include alcohols such as isopropyl alcohol and butanol; aromatic hydrocarbons such as benzene, toluene and xylene; ketones such as methyl ethyl ketone and methyl isobutyl ketone; and esters such as ethyl acetate and isobutyl acetate. These may be used singly or two or more may be suitably combined and used together. The reaction is preferably carried out at a temperature of between 50 and 180° C., and especially between 60 and 120° C. Under these temperature conditions, the reaction can be brought to substantial completion in from about 5 to about 10 hours. Because acrylic monomer is present in the copolymer solution following the reaction, this may be driven off by heating under reduced pressure. In cases where the acrylic monomer cannot be completely driven off in this way, distillation and removal is possible by adding a solvent and again heating under reduced pressure.

[Component (B)]

The volatile oil is one that can be used in cosmetic products. Use can be made of a volatile oil that is suitably selected from among those having a boiling point at normal pressure/25° C. of 260° C. or less. Exemplary volatile oils include silicone oils, hydrocarbon oils and ester oils. These may be used singly or two or more may be suitably combined and used together. Of these, from the standpoint of versatility, silicone oils and hydrocarbon oils are preferred.

The silicone oil used is one having a viscosity at 25° C. of 2 mm²/s or less. This viscosity, which is the kinematic viscosity, is a value measured at 25° C. with an Ostwald viscometer (the same applies below). At a viscosity greater than 2 mm²/s, silicone oil does not readily volatize at 25° C. and remains in the film, giving rise to a sticky sensation when included in cosmetic preparations. Examples of silicone oils include those of the following general formulas.

[Chem. 12]

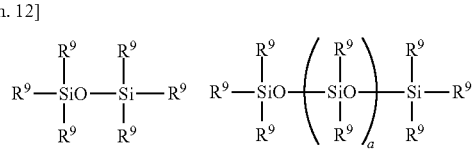

-continued

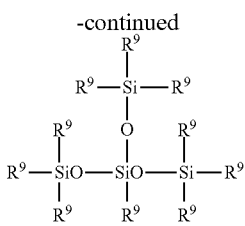

(wherein the subscript "a" is an integer from 1 to 3, and each $R^9$ is independently selected from among monovalent hydrocarbon groups and exemplified in the same way as $R^1$ above.)

Hydrocarbon oils are exemplified by volatile hydrocarbon oils that are linear or branched. Specific examples include isododecane, α-olefin oligomers, light isoparaffin, light liquid isoparaffin, liquid paraffin and liquid isoparaffin. These should be suitably selected according to, for example, the required feeling upon use. However, from the standpoint of versatility, isododecane and isoparaffin are preferred.

Examples of ester oils include ethyl acetate, butyl acetate and isopropyl acetate.

[Component (C)]

The polyoxyethylene sorbitan fatty acid ester having an average number of moles of added ethylene oxide (EO) of at least 10 and a hydrophilic-lipophilic balance (HLB) or at least 11 may be used singly or two or more may be suitably combined and used together. By using such a sorbitan fatty acid ester, an oil-in-water emulsion composition that has little bitterness, is mild, and has good coating properties, film formability and shelf stability can be achieved.

Illustrative examples of the polyoxyethylene sorbitan fatty acid ester include polyoxyethylene sorbitan monolaurate, polyoxyethylene sorbitan monostearate, polyoxyethylene sorbitan monooleate, polyoxyethylene sorbitan monopalmitate, polyoxyethylene sorbitan isostearate, polyoxyethylene sorbitan trioleate and polyoxyethylene sorbitan tristearate. Of these, from the standpoint of emulsifiability, polyoxyethylene sorbitan monolaurate, polyoxyethylene sorbitan monostearate, polyoxyethylene sorbitan monooleate and polyoxyethylene sorbitan monopalmitate are preferred. From the standpoint of bitterness and the like, polyoxyethylene sorbitan monostearate, polyoxyethylene sorbitan monooleate and polyoxyethylene sorbitan monopalmitate are more preferred. Polyoxyethylene sorbitan monolaurate, polyoxyethylene sorbitan monostearate and polyoxyethylene sorbitan monooleate are recognized also as food additives.

The number of moles of ethylene oxide added is at least 10, preferably from 10 to 100, and more preferably from 15 to 80. When the number of moles of ethylene oxide added is less than 10, the polyoxyethylene fatty acid ester dissolves the acrylic-silicone copolymer and remains in the acrylic-silicone copolymer film; hence, there is a risk of decreased film formability and of stickiness. At more than 100, it becomes solid at room temperature and is difficult to handle.

The HLB is at least 11, preferably from 13 to 18, and more preferably from 14 to 17. The HLB is determined by Griffin's formula. When a liquid surfactant having an HLB of less than 11 is included, the surfactant dissolves the acrylic-silicone copolymer and remains in the acrylic-silicone copolymer film; hence, there is a risk of decreased film formability and of stickiness.

In general, surfactants which have a low molecular weight or which have functional groups such as amino groups or include much salt are known to give rise to irritation of the skin and bitterness. Therefore, to further reduce the bitterness of an oil-in-water emulsion composition obtained by the production method of the invention, it is desirable to select a polyoxyethylene sorbitan fatty acid ester for which the content of salt and low-molecular-weight compounds is even lower. For example, it is possible to reduce the bitterness of the emulsion composition by using Nonion ST-60 or Nonion OT-80 from NOF Corporation.

[Component (D)]

Purified water or the like may be suitably selected and used as the water.

[Component (E)]

It is preferable to include (E) a water-soluble polymer compound in the oil-in-water emulsion composition of the invention in order to hold down film stickiness, increase film strength and increase emulsifiability, or in order to thicken the oil-in-water emulsion composition and increase shelf stability. "Water-soluble polymeric compound" refers to a polymer compound which has polar groups on the molecule and is dispersible in water. The water-soluble polymer compound may be a natural polymer, a semi-synthetic product or a synthetic product. Specific examples include starch, mannan, galactan from seaweeds, alginates, gum arabic, dextran, gelatin, casein, collagen, polyvinyl alcohol, methylcellulose, carboxymethylcellulose hydroxymethylcellulose, polyvinyl pyrrolidone, xanthan gum and acrylic acid polymers.

The contents of the various ingredients in the oil-in-water emulsion composition are described below.

The component (A) content is from 5 to 35 wt %, preferably from 10 to 30 wt %, and more preferably from 10 to 25 wt %. At a content lower than 5 wt %, properties such as water repellency are difficult to obtain when component (A) is included in a cosmetic preparation. On the other hand, at a content greater than 35 wt %, it is difficult to achieve a small particle size and the stability of oil-in-water emulsion compositions produced according to this invention worsens, resulting in separation over time.

The component (B) content is from 5 to 35 wt %, and preferably from 15 to 35 wt %. Because component (A) is a solid and is difficult to emulsify, preliminary dissolution in component (B) followed by emulsification is preferred. At a content lower than 5 wt %, there is a risk that component (A) will not dissolve, making emulsification impossible. On the other hand, at a content greater than 35 wt %, the volatile oil used as component (B) remains present, and so film properties when the emulsion composition is included in a cosmetic preparation cannot be obtained.

The weight ratio in which components (A) and (B) are included, expressed as (A)/(B), is preferably from 15/85 to 50/50, and more preferably from 20/80 to 45/55. Setting (A)/(B) to 15/85 or more enables properties such as water repellency to be achieved when the emulsion composition is included in a cosmetic preparation; setting (A)/(B) to 50/50 or less enables the size of the emulsion particles to be made finer, further enhancing stability over time. In addition, the viscosity (at 25° C.) of the mixed solution of components (A) and (B) is preferably not more than 500 mm²/s, more preferably not more than 300 mm²/s, and even more preferably not more than 100 mm²/s. The lower limit, although not particularly defined, may be set to 10 mm²/s or more. By setting this viscosity to not more than 500 mm²/s, the size of the emulsion particles can be made finer, further enhancing the stability over time.

The component (C) content is from 2 to 15 wt %, and preferably from 3 to 10 wt %. At a content below 2 wt %, the emulsifiability decreases and component (A) cannot be emulsified. On the other hand, at more than 15 wt %, the water repellency of the film decreases.

The component (D) content is from 15 to 88 wt %, more preferably from 20 to 75 wt %, and even more preferably from 30 to 70 wt %. At less than 15 wt %, the viscosity of the oil-in-water emulsion composition obtained by the production method of the invention rises, making the composition difficult to handle. On the other hand, at more than 88 wt %, the deionized water serving as component (D) tends to remain, making the film properties difficult to achieve.

Component (E) is an optional ingredient. When included, the amount thereof is preferably from 0.1 to 5 wt %, and more preferably from 0.2 to 3 wt %, relative to the combined amount of components (A) and (B). By setting the content of component (E) relative to the combined amount of components (A) and (B) to at least 0.1 wt %, the advantageous effects of including component (E) can be obtained. When the amount is set to more than 5 wt %, the film may become too hard and a film having the softness characteristic of acrylic-silicone graft copolymers may not be attainable.

[Optional Ingredients]

Antimicrobial agents and preservatives such as surfactants, oxazoline compounds and aromatic carboxylates, flavors, antioxidizing agents, rust inhibitors, dyes, fillers, curing catalysts, organic powders, inorganic powders and the like may be included in the oil-in-water emulsion compositions produced by the method of the invention. These may be used singly or two or more may be suitably combined and included in a suitable amount.

[Production Method]

The production method of this invention includes agitating and thereby emulsifying a composition containing above components (A), (B), (C) and (D) (Step (I)), and subsequently treating the emulsified composition under a high shear pressure of from 30 to 300 MPa (Step (II)). More preferred examples are described in detail below.

(I) Emulsification Step

Because component (A) is a solid and thus difficult to emulsify, it is preferable to first dissolve it in component (B) and then carry out emulsification. Some or all of component (C) and some or all of component (D) are added to the resulting mixed solution, and emulsification is carried out with an agitator such as a homogenizing mixer or a homogenizing disperser. Where necessary, the remaining amounts of components (C) and (D) are then added and diluted with an agitator such as a homogenizing mixer or a homogenizing disperser, thereby giving an emulsion composition (I).

The emulsification temperature is not particularly limited, although it is desirable to set it or below the flash point of the oil-in-water emulsion composition obtained by the production method of the invention. The emulsification temperature is preferably from 0 to 80° C., and more preferably from 0 to 40° C. By setting it to from 0 to 80° C., emulsification is easy and the emulsion composition becomes more stable. The stirring speed is preferably from 100 to 10,000 rpm, and more preferably from 500 to 5,000 rpm. The emulsification time is not particularly limited, although it is preferably from 1 to 60 minutes when production is carried out with a batch-type emulsifier, and is preferably 1 minute or less when production is carried out with a continuous emulsifier. The pressure during emulsification is not limited to normal pressure; that is, emulsification may also be carried out under reduced pressure or applied pressure. In cases where agitation is carried out under reduced pressure or applied pressure, bubble incorporation is sometimes discouraged, enabling more effective emulsification. When the system is set to a reduced pressure, this pressure is made higher than the vapor pressure of the starting materials so as to prevent volatilization of the starting materials.

In cases where some or all of component (C) and some of component (D) are added and emulsification is carried out with an agitator such as a homogenizing mixer or a homogenizing disperser, following which the remainder of component (D) and, if necessary, the remainder of component (C) are added and dilution is carried out, the stirring speed during dilution is preferably from 100 to 10,000 rpm, and more preferably from 500 to 5,000 rpm. The dilution time is preferably from 1 to 60 minutes when using a batch-type apparatus and 1 minute or less when using a continuous apparatus.

At a content of initially added component (D) that is low relative to the mixed solution of components (A) and (B), the average particle size of the resulting emulsion composition (I) becomes finer and, even when the shear pressure in the subsequent high shear pressure treatment is low, an oil-in-water emulsion composition of the desired particle size can be obtained. However, when the content of initially added component (D) is too small, the mixed solution of components (A) and (B) cannot be emulsified into an oil-in-water system. In light of these points, the content of initially added component (D) is preferably from 5 to 60 wt %, and more preferably from 5 to 50 wt %, of the mixed solution of components (A) and (B).

Emulsifiers that may be used include, for example, the Homogenizing Mixer (Primix Corporation), the Homogenizing Disper (Primix Corporation), the Agi Homo Mixer (Primix Corporation), the Combi Mix (Primix Corporation)—which is a three-shaft dispersion mixer that combines the Homogenizing Mixer, the Homogenizing Disper and the Anchor Mixer, a colloid mill having an agitating mechanism consisting of a rotor and a stator (such as those available from IKA, PUC, Nissei Corporation and Iwaki Co., Ltd.), high-shear mixers (such as those available from Silverson and Primix Corporation) and the Hivis Disper Mix model 3D-5 (Primix Corporation), which is an agitator based on the orbital revolution and own-axis rotation of two blades and the high-speed rotation of a toothed blade.

Emulsion particles in the emulsion composition (I) following completion of the emulsification step (I) have an average particle size that is preferably in the range of 150 to 10,000 nm.

(II) High Shear Pressure Treatment Step

The resulting emulsion composition (I) is then treated at a high shear pressure of from 30 to 300 MPa in a high-pressure homogenizing disperser, thereby giving oil-in-water emulsion composition (II). The shear pressure is from 30 to 300 MPa, and preferably from 30 to 150 MPa. At a shear pressure below 30 MPa, it is difficult to achieve an average particle size for the resulting oil-in-water emulsion composition of 300 nm or less. On the other hand, setting the shear pressure to more than 300 MPa is unlikely to have the effect of making the average particle size even smaller and moreover places a large strain on the equipment. When high shear pressure treatment does not achieve the target average particle size in a single pass, treatment may be carried out two or more times.

The high-pressure homogenizer may be a slit passage-type apparatus which emulsifies a sample by utilizing the energy of, for example, collisions between particles that form by pressurizing a mixture and ejecting it from a slit, shear forces due to pressure differences, and collisions with an impact ring; or a frontal collision-type apparatus which causes a sample to collide and emulsify by utilizing the fact that applying pressure increases acceleration. Exemplary high-pressure homogenizers include the Starburst and SUGINO HJP-25001 from Sugino Machine Ltd., the LAB1000 from SMT Co., Ltd., the HPH from IKA and the Econizer Labo-02 from Sanmaru Machinery Co., Ltd.

Component (E), in cases where other optional ingredients are included, is not particularly limited. When component (E) is included, it may be added in step (I) or may be added after high shear pressure treatment has been carried out in step (II). In cases where component (E) is added following high shear pressure treatment in step (II), mixture is carried out using an agitator such as a homogenizing mixer or a homogenizing disperser.

[Oil-in-Water Emulsion Composition]

The properties of oil-in-water emulsion compositions obtained by the production method of the invention are described. The emulsion particles are rendered to a small size by the production method of the invention. Oil-in-water emulsion compositions obtained by the production method of the invention have a good shelf stability, excellent coating properties and also excellent film formability. The film has water resistance and also has the softness characteristic of acrylic-silicone graft copolymers. When an oil-in-water emulsion composition obtained by the production method of the invention is used in a cosmetic product, a film that is mild to the skin, has little bitterness and is soft can be obtained.

The viscosity of the oil-in-water emulsion composition, although not particularly specified, is preferably from 5 to 20,000 mPa·s, more preferably from 10 to 5,000 mPa·s, and even more preferably from 30 to 2,000 mPa·s. At a viscosity of 5 mPa·s or more, the coating properties improve further; at a viscosity of 20,000 mPa·s or less, the handleability is better and the particle size becomes finer with high shear pressure treatment. The viscosity is a value measured at 25° C. with a BM-type rotational viscometer.

The emulsion particles in the oil-in-water emulsion composition have an average size of preferably 300 nm or less, and more preferably 250 nm or less. When the average particle size is larger than 300 nm, separation may soon arise. Although the average particle size has no particular lower limit, it is generally at least 100 nm, and especially at least 150 mm. The average particle size is measured by a dynamic light scattering method. The instrument used for the dynamic light scattering method is exemplified by the N4 PLUS (BECKMAN COULTER), the DelsaMax CORE (BECKMAN COULTER) and the DelsaMax Pro (BECKMAN COULTER). Measurement is carried out after diluting the oil-in-water emulsion composition with water to the optimal concentration for the particular instrument used. The method of calculating the particle size is based on the scattering intensity.

[Cosmetic Preparations]

The oil-in-water emulsion composition obtained by the production method can be included in a cosmetic preparation. The cosmetic preparation is not particularly limited and can be used in, for example, skin care cosmetics and hair care cosmetics. Based on the properties of the invention, inclusion in makeup cosmetics and skin care cosmetics is especially preferred. Examples of makeup cosmetics include foundation (including all solid and liquid foundations), cream, makeup base, skin milk, eyeshadow, lipstick, lip cream, rouge, eyebrow, mascara, eyeliner, cleansing preparations and packs. Of these, lipsticks are preferred. The form of the cosmetic preparation is not particularly limited. For example, various forms such as liquids, emulsions, creams, solids, pastes, gels, multilayer preparations, mousses, sprays, sticks and pencils may be selected. The content of the oil-in-water emulsion composition therein is preferably from 1 to 70 wt %, and more preferably from 3 to 50 wt %. The advantageous effects of the invention are readily obtained particularly within this range. When the content is too high, a heavy texture may result.

Various ingredients used in conventional cosmetic preparations may be included in cosmetic preparations containing the oil-in-water emulsion composition of the invention, within ranges that do not detract from the advantageous effects of the invention. For example, the following may be included as ingredients: oils, alcoholic hydroxyl group-containing compounds, surfactants, powders, compositions of a crosslinked organopolysiloxane and an oil that is liquid at room temperature, silicone wax, film-forming agents, antiperspirants, antimicrobial agents and other additives. These may be used singly or two or more may be suitably combined and used together.

EXAMPLES

The invention is illustrated more fully below by way of Examples and Comparative Examples, although the invention is not limited by these Examples. In the following Examples, unless noted otherwise, references to "%" in the composition signify percent by weight, and references to "ratios" signify weight ratios. The dynamic viscosity is a measured value obtained at 25° C. with an Ostwald viscometer.

Synthesis Example 1

A toluene solution of component (A-1) an acrylic-silicone copolymer of structural formula (11) below was obtained by mixing together 100 g of a monomethacrylate-terminated dimethylpolysiloxane of formula (10) below, 80 g of methyl methacrylate, 20 g of 2-ethylhexyl acrylate and 200 g of toluene, subsequently adding and dissolving 2 g of t-butylperoxy-2-ethylhexyl hexanoate (NOF Corporation, Perbutyl O), and then reacting for 10 hours under a nitrogen atmosphere and in a temperature range of between 90 and 100° C. The polystyrene-equivalent weight-average molecular weight determined by GPC (toluene) was about 25,000.

[Chem. 13]

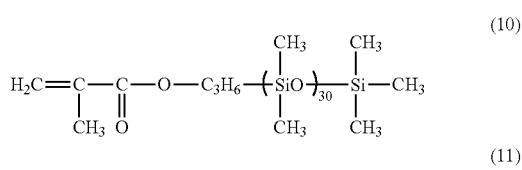

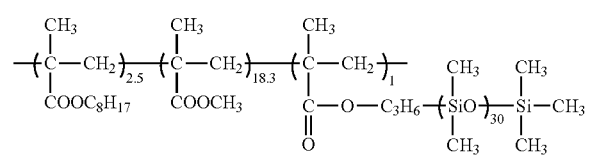

Constituent unit molar ratio (1)/(2)=1/(2.5+18.3)=0.05

Four hundred grams of the toluene solution of the copolymer of formula (11) was heated under reduced pressure at 130° C. and 10 mmHg, driving off the toluene and acrylic monomer, following which 200 g of isododecane was added and heating was carried out under reduced pressure at 130° C. and 10 mmHg, driving off the isododecane and the acrylic monomer. Next, 370 g of (B-1) isododecane was added and the acrylic-silicone copolymer (A-1) was dissolved, giving Mixed Solution (i). The ratio expressed as (A-1)/(B-1) was about 35/65, and the viscosity (25° C.) of Mixed Solution (i) was 80 mm²/s. The methyl methacrylate and 2-ethylhexyl acrylate contents were each less than 10 ppm.

Synthesis Example 2

Four hundred grams of the toluene solution of acrylic-silicone copolymer (A) obtained in Synthesis Example 1 was heated under reduced pressure at 130° C. and 10 mmHg, driving off the toluene and the acrylic monomer, following which 200 g of isododecane was added and heating under reduced pressure was carried out at 130° C. and 10 mmHg, driving off the isododecane and the acrylic monomer. Next, 300 g of (B-1) isododecane was added and the (A) acrylic-silicone copolymer was dissolved, giving Mixed Solution (ii). The ratio expressed as (A-1)/(B-1) was about 40/60, and the viscosity (25° C.) of Mixed Solution (ii) was 320 mm²/s. The methyl methacrylate and 2-ethylhexyl acrylate were each less than 10 ppm.

Synthesis Example 3

Four hundred grams of the toluene solution of acrylic-silicone copolymer (A) obtained in Synthesis Example 1 was heated under reduced pressure at 130° C. and 10 mmHg, driving off the toluene and the acrylic monomer, following which 200 g of isododecane was added and heating under reduced pressure was carried out at 130° C. and 10 mmHg, driving off the isododecane and the acrylic monomer. Next, 470 g of the silicone compound of formula (12) below as component (B-2) was added and the (A) acrylic-silicone copolymer was dissolved, giving Mixed Solution (iii). The ratio expressed as (A-1)/(B-2) was about 30/70, and the viscosity (25° C.) of Mixed Solution (iii) was 40 mm²/s. The methyl methacrylate and 2-ethylhexyl acrylate contents were each less than 10 ppm.

[Chem. 14]

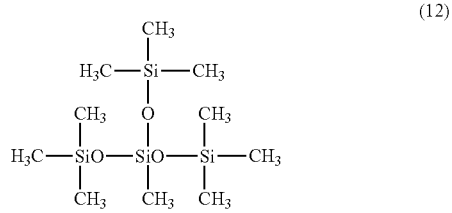

(12)

Example 1

Fifty grams of (C-1) Nonion OT-80 (polyoxyethylene (20 EO) sorbitan monooleate; HLB, 15.7; from NOF Corporation) and 150 g of (D) deionized water were added to 500 g of Mixed Solution (i) and emulsification was carried out by stirring for 10 minutes at 5,000 rpm with the T.K. Homogenizing Mixer (Primix Corporation), following which 300 g of (D) deionized water was added and stirring was carried out for 3 minutes at 2,000 rpm with the T.K. Homogenizing Mixer (Primix Corporation), thereby giving Emulsion Composition (I-1). Emulsion Composition (I-1) had an average particle size, as measured with the N4 PLUS (BECKMAN COULTER), of 3,000 nm. Emulsion Composition (I-1) was then treated twice at 100 MPa with the SUGINO HJP-25001 (Sugino Machine Ltd.), giving Oil-in-Water Emulsion Composition (II-1). Oil-in-Water Emulsion Composition (II-1) had a viscosity of 900 mPa·s and an average particle size, as determined with the N4 PLUS (BECKMAN COULTER), of 220 nm.

Example 2

Fifty grams of (C-1) Nonion OT-80 (polyoxyethylene (20 EO) sorbitan monooleate; HLB, 15.7; from NOF Corporation) and 150 g of (D) deionized water were added to 500 g of Mixed Solution (ii) and emulsification was carried out by stirring for 10 minutes at 5,000 rpm with the T.K. Homogenizing Mixer (Primix Corporation), following which 300 g of (D) deionized water was added and stirring was carried out for 3 minutes at 2,000 rpm with the T.K. Homogenizing Mixer (Primix Corporation), thereby giving Emulsion Composition (I-2). Emulsion Composition (I-2) had an average particle size, as measured with the N4 PLUS (BECKMAN COULTER), of 1,600 nm. Emulsion Composition (I-2) was then treated twice at 100 MPa with the SUGINO HJP-25001 (Sugino Machine Ltd.), giving Oil-in-Water Emulsion Composition (II-2). Oil-in-Water Emulsion Composition (II-2) had a viscosity of 300 mPa·s and an average particle size, as determined with the N4 PLUS (BECKMAN COULTER), of 230 nm.

Example 3

Fifty grams of (C-2) Nonion ST-60 (polyoxyethylene (20 EO) sorbitan monostearate; HLB, 15.7; from NOF Corporation) and 150 g of (D) deionized water were added to 500 g of Mixed Solution (i) and emulsification was carried out by stirring for 10 minutes at 5,000 rpm with the T.K. Homogenizing Mixer (Primix Corporation), following which 300 g of (D) deionized water was added and stirring was carried out for 3 minutes at 2,000 rpm with the T.K. Homogenizing Mixer (Primix Corporation), thereby giving Emulsion Composition (I-3). Emulsion Composition (I-3) had an average particle size, as measured with the N4 PLUS (BECKMAN COULTER), of 3,800 nm. Emulsion Composition (I-3) was then treated twice at 100 MPa with the SUGINO HJP-25001 (Sugino Machine Ltd.), giving Oil-in-Water Emulsion Composition (II-3). Oil-in-Water Emulsion Composition (II-3) had a viscosity of 700 mPa·s and an average particle size, as determined with the N4 PLUS (BECKMAN COULTER), of 220 nm.

Example 4

Fifty grams of (C-1) Nonion OT-80 (polyoxyethylene (20 EO) sorbitan monooleate; HLB, 15.7; from NOF Corporation) and 150 g of (D) deionized water were added to 500 g of Mixed Solution (iii) and emulsification was carried out by stirring for 10 minutes at 5,000 rpm with the T.K. Homogenizing Mixer (Primix Corporation), following which 300 g of (D) deionized water was added and stirring was carried out for 3 minutes at 2,000 rpm with the T.K. Homogenizing Mixer (Primix Corporation), thereby giving Emulsion Composition (I-4). Emulsion Composition (I-4) had an average particle size, as measured with the N4 PLUS (BECKMAN COULTER), of 3,100 nm. Emulsion Composition (I-4) was then treated twice at 100 MPa with the SUGINO HJP-25001 (Sugino Machine Ltd.), giving Oil-in-Water Emulsion Composition (II-4). Oil-in-Water Emulsion Composition (II-4)

had a viscosity of 1,200 mPa·s and an average particle size, as determined with the N4 PLUS (BECKMAN COULTER), of 230 nm.

Example 5

Fifty grams of (C-1) Nonion OT-80 (polyoxyethylene (20 EO) sorbitan monooleate; HLB, 15.7; from NOF Corporation), 33 g of (E) a 15% aqueous solution (Poval, from Japan Vam & Poval Co., Ltd.) of Gohsenol EG-40C (polyvinyl alcohol) and 122 g of (D) deionized water were added to 500 g of Mixed Solution (i) and emulsification was carried out by stirring for 10 minutes at 5,000 rpm with the T.K. Homogenizing Mixer (Primix Corporation), following which 295 g of (D) deionized water was added and stirring was carried out for 3 minutes at 2,000 rpm with the T.K. Homogenizing Mixer (Primix Corporation), thereby giving Emulsion Composition (I-5). Emulsion Composition (I-5) had an average particle size, as measured with the N4 PLUS (BECKMAN COULTER), of 3,600 nm. Emulsion Composition (I-5) was then treated twice at 100 MPa with the SUGINO HJP-25001 (Sugino Machine Ltd.), giving Oil-in-Water Emulsion Composition (II-5). Oil-in-Water Emulsion Composition (II-5) had a viscosity of 5,000 mPa·s and an average particle size, as determined with the N4 PLUS (BECKMAN COULTER), of 280 nm.

Example 6

Fifty grams of (C-2) Nonion ST-60 (polyoxyethylene (20 EO) sorbitan monostearate; HLB, 15.7; from NOF Corporation) and 150 g of (D) deionized water were added to 500 g of Mixed Solution (i) and emulsification was carried out by stirring for 10 minutes at 5,000 rpm with the T.K. Homogenizing Mixer (Primix Corporation), following which 300 g of (D) deionized water was added and stirring was carried out for 3 minutes at 2,000 rpm with the T.K. Homogenizing Mixer (Primix Corporation), thereby giving Emulsion Composition (I-6). Emulsion Composition (I-6) had an average particle size, as measured with the N4 PLUS (BECKMAN COULTER), of 1,400 nm. Emulsion Composition (I-6) was then treated once at 70 MPa with the SUGINO HJP-25001 (Sugino Machine Ltd.), giving Oil-in-Water Emulsion Composition (II-6). Oil-in-Water Emulsion Composition (II-6) had a viscosity of 350 mPa·s and an average particle size, as determined with the N4 PLUS (BECKMAN COULTER), of 270 nm.

Comparative Example 1

Fifty grams of (C-1) Nonion OT-80 (polyoxyethylene (20 EO) sorbitan monooleate; HLB, 15.7; from NOF Corporation) and 150 g of (D) deionized water were added to 500 g of Mixed Solution (i) and emulsification was carried out by stirring for 10 minutes at 5,000 rpm with the T.K. Homogenizing Mixer (Primix Corporation), following which 300 g of (D) deionized water was added and stirring was carried out for 3 minutes at 2,000 rpm with the T.K. Homogenizing Mixer (Primix Corporation), thereby giving Emulsion Composition (I-7). Emulsion Composition (I-7) had a viscosity of 300 mPa·s and an average particle size, as measured with the N4 PLUS (BECKMAN COULTER), of 1,600 nm.

Comparative Example 2

Fifty grams of (C-1) Nonion OT-80 (polyoxyethylene (20 EO) sorbitan monooleate; HLB, 15.7; from NOF Corporation) and 60 g of (D) deionized water were added to 500 g of Mixed Solution (i) and emulsification was carried out by stirring for 45 minutes at 2,000 rpm with the T.K. Homogenizing Mixer (Primix Corporation), following which 390 g of (D) deionized water was added and stirring was carried out for 3 minutes at 2,000 rpm with the T.K. Homogenizing Mixer (Primix Corporation), thereby giving Emulsion Composition (I-8). Emulsion Composition (I-8) had a viscosity of 700 mPa·s and an average particle size, as measured with the N4 PLUS (BECKMAN COULTER), of 550 nm.

Comparative Example 3

Thirty grams of (C-3) Emulgen 104P (polyoxyethylene (4) lauryl ether; from Kao Corporation), 20 g of (C-4) Emulgen 123P (polyoxyethylene (23) lauryl ether; Kao Corporation) and 150 g of (D) deionized water were added to 500 g of Mixed Solution (i) and emulsification was carried out by stirring for 10 minutes at 5,000 rpm with the T.K. Homogenizing Mixer (Primix Corporation), following which 300 g of (D) deionized water was added and stirring was carried out for 3 minutes at 2,000 rpm with the T.K. Homogenizing Mixer (Primix Corporation), thereby giving Emulsion Composition (I-9). Emulsion Composition (I-9) had an average particle size, as measured with the N4 PLUS (BECKMAN COULTER), of 700 nm. Emulsion Composition (I-9) was then treated twice at 100 MPa with the SUGINO HJP-25001 (Sugino Machine Ltd.), giving Oil-in-Water Emulsion Composition (II-8). Oil-in-Water Emulsion Composition (II-8) had a viscosity of 230 mPa·s and an average particle size, as determined with the N4 PLUS (BECKMAN COULTER), of 270 nm.

Comparative Example 4

Twenty-eight grams of (C-5) NIKKOL Decaglyn 1-LV (polyglyceryl monolaurate; from Nikko Chemical Co., Ltd.), 22 g of (C-6) NIKKOL Decaglyn 1-ISV EX (polyglyceryl monoisostearate; Nikko Chemical Co., Ltd.) and 150 g of (D) deionized water were added to 500 g of Mixed Solution (i) and stirring was carried out for 10 minutes at 5,000 rpm with the T.K. Homogenizing Mixer (Primix Corporation), following which 300 g of (D) deionized water was added and emulsification was carried out by stirring for 1 minute at 2,000 rpm with the T.K. Homogenizing Mixer (Primix Corporation), thereby giving Emulsion Composition (I-10). Emulsion Composition (I-10) had an average particle size, as measured with the N4 PLUS (BECKMAN COULTER), of 4,200 nm. Emulsion Composition (I-10) was then treated twice at 100 MPa with the SUGINO HJP-25001 (Sugino Machine Ltd.), giving Oil-in-Water Emulsion Composition (II-10). Oil-in-Water Emulsion Composition (II-10) had a viscosity of 500 mPa·s and an average particle size, as determined with the N4 PLUS (BECKMAN COULTER), of 240 nm.

The ingredient makeup, average particle size, viscosity and results of evaluations on shelf stability, presence/absence of bitterness, coatability (coating properties), and film formability of Oil-in-Water Emulsion Compositions II-1 to II-10 and Emulsion Compositions I-6 and I-7 obtained in the above Examples are shown in the tables below.

The average particle sizes are measured values obtained with the N4 PLUS (BECKMAN COULTER), and the viscosities of the compositions are values measured at 25° C. with a BM-type rotational viscometer. The compositions in the Examples of the invention formed films having the softness characteristic of acrylic-silicone graft copolymers and were not irritating to the skin.

[Shelf Stability]

A 100 g amount of the emulsion composition was placed in a glass bottle (volume, 125 mL) and left at rest for one month, following which the nonvolatile contents (105° C., 3 hours) of the top layer and the bottom layer were measured. The result is indicated as the value obtained by dividing the nonvolatile content of the top layer by the nonvolatile content of the bottom layer. The more this value diverges from unity, the greater the degree of separation.

[Bitterness]

The bitterness was evaluated by five subjects who spread 0.1 g of the emulsion composition on the back of their hand, dried the composition at room temperature, and then licked this area and rated the bitterness according to the following criteria. The results, averaged for the five subjects, are indicated as "○" or "X".

<Evaluation Criteria for Bitterness>
5: Substantially or entirely free of bitterness
1: Some bitterness <Rating Criteria for Bitterness>
O: Average value was 3 or more
X: Average value was less than 3

[Coatability]

The emulsion composition was applied to a weight of 100 g/m² onto uncoated paperboard (10 cm×14 cm) using a 100 μm film thickness bar coater, and was evaluated for crawling.

<Rating Criteria for Coatability>
○: No crawling, or crawling occurs on less than 30% of overall coated surface
Δ: Crawling occurs on at least 30% but less than 50% of overall coated surface
X: Crawling occurs on at least 50% of overall coated surface
A rating of "Δ" or "○" is acceptable.

[Film Formability]

Two grams of the emulsion composition was placed in a 6 cm diameter aluminum Petri dish, dried for 24 hours at room temperature, and the condition of the film was examined.

<Rating Criteria for Film Formability>
○: A continuous film forms
X: Film does not peel from aluminum Petri dish and fails to form a continuous film

[Water Resistance]

Two grams of the emulsion composition was placed in a 6 cm diameter aluminum Petri dish and dried for 24 hours at room temperature. A single drop of water was deposited with a pipette on the formed film and the water was lightly wiped off 10 seconds later, after which the condition of the film was examined.

<Rating Criteria for Water Resistance>
○: No change in film
X: Surface whitens or part of the film peels off

TABLE 1

| Composition (%) | | Example | | | | | |
|---|---|---|---|---|---|---|---|
| | | 1 | 2 | 3 | 4 | 5 | 6 |
| Component (A) | (A-1) | 17.5 | 20.0 | 17.5 | 15.0 | 17.5 | 17.5 |
| Component (B) | (B-1) | 32.5 | 30.0 | 32.5 | | 32.5 | 32.5 |
| | (B-2) | | | | 35.0 | | |
| Component (C) | (C-1) | 5.0 | 5.0 | | 5.0 | 5.0 | |
| | (C-2) | | | 5.0 | | | 5.0 |
| Component (D) | | 45.0 | 45.0 | 45.0 | 45.0 | 44.5 | 45.0 |
| Component (E) | | 0 | 0 | 0 | 0 | 0.5 | 0 |
| Total | | 100 | 100 | 100 | 100 | 100 | 100 |
| Emulsion composition | | II-1 | II-2 | II-3 | II-4 | II-5 | II-6 |
| Use of high-pressure treatment during production | | yes | yes | yes | yes | yes | yes |
| Average particle size (nm) | | 220 | 230 | 220 | 230 | 280 | 270 |
| Viscosity (mPa · s) | | 900 | 300 | 700 | 1,200 | 5,000 | 350 |
| Shelf stability: nonvolatile content of upper layer/nonvolatile content of lower layer | Room temperature | 1.01 | 1.00 | 1.01 | 1.02 | 1.00 | 1.03 |
| | 40° C. | 1.00 | 1.00 | 0.99 | 1.02 | 1.02 | 1.03 |
| Bitterness | | ○ | ○ | ○ | ○ | ○ | ○ |
| Coatability | | ○ | ○ | ○ | ○ | ○ | ○ |
| Film formability | | ○ | ○ | ○ | ○ | ○ | ○ |
| Water resistance | | ○ | ○ | ○ | ○ | ○ | ○ |

TABLE 2

| Composition (%) | | Comparative Example | | | |
|---|---|---|---|---|---|
| | | 1 | 2 | 3 | 4 |
| Component (A) | (A-1) | 17.5 | 17.5 | 17.5 | 17.5 |
| Component (B) | (B-1) | 32.5 | 32.5 | 32.5 | 32.5 |
| Component (C) | (C-1) | 5.0 | 5.0 | | |
| | (C-3) | | | 3.0 | |
| | (C-4) | | | | 2.0 |

TABLE 2-continued

|  | | Comparative Example | | | |
|---|---|---|---|---|---|
| Composition (%) | | 1 | 2 | 3 | 4 |
| (C-5) | | | | | 2.8 |
| (C-6) | | | | | 2.2 |
| Component (D) | | 45.0 | 45.0 | 45.0 | 45.0 |
| Total | | 100 | 100 | 100 | 100 |
| Emulsion composition | | I-7 | I-8 | II-9 | II-10 |
| Use of high-pressure treatment during production | | no | no | yes | yes |
| Average particle size (nm) | | 1,600 | 550 | 230 | 240 |
| Viscosity (mPa · s) | | 300 | 700 | 1,100 | 500 |
| Shelf stability: nonvolatile content of upper layer/ | Room temperature | 2.56 | 1.29 | 1.01 | 1.01 |
| nonvolatile content of lower layer | 40° C. | 4.23 | 2.25 | 0.94 | 1.04 |
| Bitterness | | ○ | ○ | X | ○ |
| Coatability | | Δ | Δ | ○ | Δ |
| Film formability | | ○ | ○ | X | X |
| Water resistance | | ○ | ○ | X | X |

[Formulation Example] Cream Lipstick

<Method of Preparation>

A: Component (8) was mixed into part of component (2) and dispersed in a roll mill, following which the resulting dispersion was heated and mixed together with components (1) to (4).

B: Components (5) to (7) were heated, added to the mixture obtained in A and emulsification was carried out, followed by cooling.

C: Component (9) was added to the emulsion composition obtained in B, giving a cream lipstick.

| | Ingredient (%) |
|---|---|
| (1) Dextrin palmitate/ethylhexanoate[1)] | 9 |
| (2) Triethylhexanoin | 5 |
| (3) Alkyl-modified branched polyglycerin-modified silicone [2)] | 2 |
| (4) Decamethylcyclopentasiloxane | 40 |
| (5) 1,3-Butylene glycol | 5 |
| (6) Emulsion Composition (II-3) from Example 3 | 15 |
| (7) Purified water | 16 |
| (8) Colorant | suitable amount |
| (9) Mica | suitable amount |
| Total | 100 |

1) Rheopearl TT, from Chiba Flour Milling Co., Ltd.

2) KF-6105, from Shin-Etsu Chemical Co., Ltd.

The resulting cream lipstick spread easily, was not sticky or oily, and formed a long-lasting film on the lips. Also, it did not leave a bitter or unpleasant sensation when applied, and was easy to use.

The invention claimed is:

1. A method for producing an oil-in-water emulsion composition, comprising the steps of:

agitating and thereby emulsifying a composition containing:

(A) from 5 to 35 wt % of an acrylic-silicone graft copolymer which has a weight-average molecular weight of 3,000 to 100,000 and contains constituent units (1) and (2) of the following general formulas

[Chem. 1]

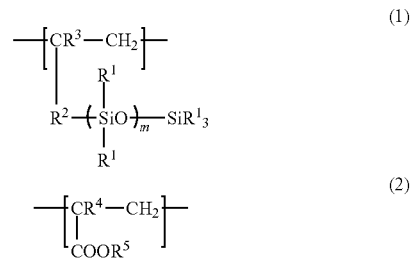

wherein each $R^1$ is a group independently selected from monovalent hydrocarbon groups, $R^2$ is an alkyleneoxycarbonyl group of 2 to 11 carbon atoms, the alkylene group being limited to a structure that bonds with a silicon atom, $R^3$ and $R^4$ are each independently a hydrogen atom or a methyl group, $R^5$ is an alkyl group of 1 to 22 carbon atoms or a hydrogen atom, m is an integer from 3 to 500, and the molar ratio between the constituent units having general formulas (1) and (2), expressed as (1)/(2), is from 0.02 to 1, (B) from 5 to 35 wt % of a volatile oil, (C) from 2 to 15 wt % of a polyoxyethylene sorbitan fatty acid ester having an average number of moles of added ethylene oxide (EO) of at least 10 and a hydrophilic-lipophilic balance (HLB) of at least 11, and (D) from 15 to 88 wt % of water; and subsequently treating the emulsified composition under a high shear pressure of from 30 to 300 MPa.

2. The method for producing an oil-in-water emulsion composition of claim 1, wherein component (C) is one or more selected from the group consisting of polyoxyethylene sorbitan monolaurate, polyoxyethylene sorbitan monostearate, polyoxyethylene sorbitan monooleate and polyoxyethylene sorbitan monopalmitate.

3. The method for producing an oil-in-water emulsion composition of claim 1, wherein emulsion particles in the oil-in-water emulsion composition have an average particle size of 300 nm or less.

4. The method for producing an oil-in-water emulsion composition of claim 1, wherein component (B) is a volatile oil selected from the group consisting of silicone oils having a viscosity at 25'C of 0.2 mm²/s or less and hydrocarbon oils.

5. The method for producing an oil-in-water emulsion composition of claim 1, further comprising the step of including (E) a water-soluble polymer compound in an amount, based on the combined amount of components (A) and (B), of from 0.1 to 5 wt %.

6. A cosmetic preparation comprising the oil-in-water emulsion composition obtained by the production method of claim 1.

* * * * *